(12) United States Patent
Malinowski

(10) Patent No.: US 11,058,870 B2
(45) Date of Patent: Jul. 13, 2021

(54) BURR HOLE PLUGS FOR ELECTRICAL STIMULATION SYSTEMS AND METHODS OF MAKING AND USING

(71) Applicant: Boston Scientific Neuromodulation Corporation, Valencia, CA (US)

(72) Inventor: Zdzislaw Bernard Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 206 days.

(21) Appl. No.: 16/292,682

(22) Filed: Mar. 5, 2019

(65) Prior Publication Data
US 2019/0275317 A1    Sep. 12, 2019

Related U.S. Application Data

(60) Provisional application No. 62/641,180, filed on Mar. 9, 2018.

(51) Int. Cl.
*A61N 1/05* (2006.01)
*A61B 90/10* (2016.01)
(Continued)

(52) U.S. Cl.
CPC ........... *A61N 1/0539* (2013.01); *A61B 90/10* (2016.02); *A61N 1/3605* (2013.01); *A61N 1/372* (2013.01);
(Continued)

(58) Field of Classification Search
CPC ........... A61B 2090/103; A61B 5/6864; A61B 2017/347; A61B 90/11; A61B 90/10;
(Continued)

(56) References Cited

U.S. PATENT DOCUMENTS

| 979,652 A | 12/1910 | Church |
| 2,186,277 A | 1/1940 | Tetens |

(Continued)

FOREIGN PATENT DOCUMENTS

| EP | 0911061 | 4/1999 |
| JP | S55-112538 | 7/1980 |

(Continued)

OTHER PUBLICATIONS

Lieberman, Daniel E. et al., Basicranial influence on overall cranial shape, Journal of Human Evolution, vol. 38 (2000) pp. 291-315.
(Continued)

*Primary Examiner* — Katherine H Schwiker
(74) *Attorney, Agent, or Firm* — Branch Partners PLLC; Bruce E. Black

(57) ABSTRACT

A burr hole plug includes a base having a flange configured to rest on the skull of a patient and a sidewall configured to extend into a burr hole. The burr hole plug also includes a flexible cover configured to be disposed entirely over, and coupled to, the base. The flexible cover includes a skirt to fit around an outer perimeter of the base and a rim that fits inside the sidewall of the base. Between the skirt and the rim is an inset region having a shape corresponding to a shape of the flange of the base. Alternatively or additionally, the burr hole plug may include two lead retention members, each of the lead retention members including a lead engagement surface to engage and hold a lead; and a locking member for locking the two lead retention members in the base.

16 Claims, 7 Drawing Sheets

(51) Int. Cl.
*A61N 1/372* (2006.01)
*A61N 1/36* (2006.01)

(52) U.S. Cl.
CPC ....... *A61B 2090/103* (2016.02); *A61N 1/0529* (2013.01); *A61N 1/0534* (2013.01)

(58) Field of Classification Search
CPC .. A61N 1/0523; A61N 1/0529; A61N 1/0531; A61N 1/0534; A61N 1/0539; A61N 1/3605; A61N 1/0526; A61M 2025/024
See application file for complete search history.

(56) References Cited

U.S. PATENT DOCUMENTS

| | | | |
|---|---|---|---|
| 2,521,301 | A | 9/1950 | Morrison |
| 2,873,822 | A | 2/1959 | Sloan |
| 2,912,712 | A | 11/1959 | Shamban et al. |
| 3,758,827 | A | 9/1973 | Schroder et al. |
| 3,826,952 | A | 7/1974 | Iwasaki et al. |
| 3,829,737 | A | 8/1974 | Johnsson |
| 4,114,603 | A | 9/1978 | Wilkinson |
| 4,245,645 | A | 1/1981 | Arseneault et al. |
| 4,297,609 | A | 10/1981 | Hirao et al. |
| 4,315,180 | A | 2/1982 | Kondo et al. |
| 4,328,313 | A | 5/1982 | Simonson et al. |
| 4,328,813 | A | 5/1982 | Ray |
| 4,467,800 | A | 8/1984 | Zytkovicz |
| 4,741,571 | A | 5/1988 | Godette |
| 4,805,634 | A | 2/1989 | Ullrich et al. |
| 4,826,487 | A | 5/1989 | Winter |
| 4,850,359 | A | 7/1989 | Putz |
| 4,931,056 | A | 6/1990 | Ghajar et al. |
| 4,955,891 | A | 9/1990 | Carol |
| 4,998,938 | A | 3/1991 | Ghajar et al. |
| 5,116,345 | A | 5/1992 | Jewell et al. |
| 5,193,539 | A | 3/1993 | Schulman et al. |
| 5,193,540 | A | 3/1993 | Schulman et al. |
| 5,201,737 | A | 4/1993 | Leibinger et al. |
| 5,235,990 | A | 8/1993 | Dempsey |
| 5,300,080 | A | 4/1994 | Clayman et al. |
| 5,324,316 | A | 6/1994 | Schulman et al. |
| 5,330,485 | A | 7/1994 | Clayman et al. |
| 5,464,446 | A | 11/1995 | Dreessen et al. |
| 5,484,445 | A | 1/1996 | Knuth |
| 5,496,356 | A | 3/1996 | Hudz |
| 5,503,164 | A | 4/1996 | Friedman |
| 5,549,620 | A | 8/1996 | Bremer |
| 5,707,373 | A | 1/1998 | Sevrain et al. |
| 5,732,699 | A | 3/1998 | Lundback |
| 5,776,144 | A | 7/1998 | Levsieffer et al. |
| 5,800,504 | A | 9/1998 | Bellifemine |
| 5,843,150 | A | 12/1998 | Dreessen et al. |
| 5,865,842 | A | 2/1999 | Knuth et al. |
| 5,891,028 | A | 4/1999 | Lundback |
| 5,897,531 | A | 4/1999 | Amirana |
| 5,916,154 | A | 6/1999 | Hobbs et al. |
| 5,927,277 | A | 7/1999 | Baudino et al. |
| 5,954,687 | A | 9/1999 | Baudino |
| 5,984,930 | A | 11/1999 | Maciunas et al. |
| 5,993,463 | A | 11/1999 | Truwit |
| 6,006,124 | A | 12/1999 | Fischell et al. |
| 6,016,449 | A | 1/2000 | Fischell et al. |
| 6,044,304 | A | 3/2000 | Baudino |
| 6,050,098 | A | 4/2000 | Meyer et al. |
| 6,050,998 | A | 4/2000 | Fletcher |
| 6,073,048 | A | 6/2000 | Kieval et al. |
| 6,094,598 | A | 7/2000 | Elsberry et al. |
| 6,117,143 | A | 9/2000 | Hynes et al. |
| 6,126,663 | A | 10/2000 | Hair |
| 6,128,537 | A | 10/2000 | Rise |
| 6,128,538 | A | 10/2000 | Fischell et al. |
| 6,134,474 | A | 10/2000 | Fischell et al. |
| 6,134,477 | A | 10/2000 | Knuteson |
| 6,171,239 | B1 | 1/2001 | Humphrey |
| 6,175,710 | B1 | 1/2001 | Kamaji et al. |
| 6,181,969 | B1 | 1/2001 | Gord |
| 6,200,329 | B1 | 3/2001 | Fung et al. |
| 6,210,417 | B1 | 4/2001 | Baudino et al. |
| 6,224,450 | B1 | 5/2001 | Norton |
| 6,230,049 | B1 | 5/2001 | Fischell et al. |
| 6,269,270 | B1 | 7/2001 | Boveja |
| 6,271,094 | B1 | 8/2001 | Boyd et al. |
| 6,284,729 | B1 | 9/2001 | Bernfield et al. |
| 6,295,944 | B1 | 10/2001 | Lovett |
| 6,321,104 | B1 | 11/2001 | Gielen et al. |
| 6,324,433 | B1 * | 11/2001 | Errico ................ A61N 1/0534 607/116 |
| 6,353,762 | B1 | 3/2002 | Baudino et al. |
| 6,354,299 | B1 | 3/2002 | Fischell et al. |
| 6,356,729 | B1 | 3/2002 | Sasaki et al. |
| 6,356,777 | B1 | 3/2002 | Garfield et al. |
| 6,356,792 | B1 | 3/2002 | Errico |
| 6,364,278 | B1 | 4/2002 | Lin et al. |
| 6,374,140 | B1 | 4/2002 | Rise |
| 6,391,985 | B1 | 5/2002 | Goode et al. |
| 6,413,263 | B1 | 7/2002 | Lobdill et al. |
| 6,427,086 | B1 | 7/2002 | Fischell et al. |
| 6,447,443 | B1 | 9/2002 | Keogh et al. |
| 6,459,936 | B2 | 10/2002 | Fischell et al. |
| 6,463,328 | B1 | 10/2002 | John |
| 6,464,687 | B1 | 10/2002 | Ishikawa et al. |
| 6,466,822 | B1 | 10/2002 | Pless |
| 6,480,743 | B1 | 11/2002 | Kirkpatrick et al. |
| 6,482,182 | B1 | 11/2002 | Carroll et al. |
| 6,516,227 | B1 | 2/2003 | Meadows |
| 6,560,486 | B1 | 5/2003 | Osorio et al. |
| 6,571,127 | B1 | 5/2003 | Ben-Haim et al. |
| 6,574,498 | B1 | 6/2003 | Gilboa |
| 6,597,954 | B1 | 7/2003 | Pless et al. |
| 6,609,020 | B2 | 8/2003 | Gill |
| 6,609,029 | B1 | 8/2003 | Mann et al. |
| 6,609,032 | B1 | 8/2003 | Woods et al. |
| 6,618,623 | B1 | 9/2003 | Pless et al. |
| 6,647,296 | B2 | 11/2003 | Fischell et al. |
| 6,690,974 | B2 | 2/2004 | Archer et al. |
| 6,741,892 | B1 | 5/2004 | Meadows et al. |
| 6,795,737 | B2 | 9/2004 | Gielen et al. |
| 6,845,257 | B2 | 1/2005 | Fuimaono et al. |
| 6,845,267 | B2 | 1/2005 | Harrison et al. |
| 6,895,280 | B2 | 5/2005 | Meadows et al. |
| 6,920,359 | B2 | 7/2005 | Meadows et al. |
| 6,944,501 | B1 | 9/2005 | Pless |
| 6,950,707 | B2 | 9/2005 | Whitehurst |
| 7,004,948 | B1 | 2/2006 | Pianca et al. |
| 7,033,326 | B1 | 4/2006 | Pianca et al. |
| 7,050,855 | B2 | 5/2006 | Zeijlemaker et al. |
| 7,090,661 | B2 | 8/2006 | Morris et al. |
| 7,118,828 | B2 | 10/2006 | Dodd et al. |
| 7,146,222 | B2 | 12/2006 | Boling |
| 7,174,213 | B2 | 2/2007 | Pless |
| 7,174,219 | B2 | 2/2007 | Wahlstrand et al. |
| 7,177,701 | B1 | 2/2007 | Pianca |
| 7,204,840 | B2 | 4/2007 | Skakoon et al. |
| 7,212,864 | B2 | 5/2007 | Wahlstrand et al. |
| 7,235,084 | B2 | 6/2007 | Skakoon et al. |
| 7,242,982 | B2 | 7/2007 | Singhal et al. |
| 7,244,150 | B1 | 7/2007 | Brase et al. |
| 7,343,205 | B1 | 3/2008 | Pianca et al. |
| 7,369,899 | B2 | 5/2008 | Malinowski et al. |
| 7,421,297 | B2 | 9/2008 | Gifakis et al. |
| 7,437,193 | B2 | 10/2008 | Parramon et al. |
| 7,450,997 | B1 | 11/2008 | Pianca et al. |
| 7,454,251 | B2 | 11/2008 | Rezai et al. |
| 7,479,146 | B2 | 1/2009 | Malinowski et al. |
| 7,548,775 | B2 | 6/2009 | Kipke et al. |
| 7,636,596 | B2 | 12/2009 | Solar |
| 7,672,734 | B2 | 3/2010 | Anderson et al. |
| 7,682,745 | B2 | 3/2010 | Howard et al. |
| 7,704,260 | B2 * | 4/2010 | Skakoon ................ A61M 25/02 606/130 |
| 7,756,922 | B2 | 7/2010 | Basu et al. |
| 7,761,165 | B1 | 7/2010 | He et al. |
| 7,766,922 | B1 | 8/2010 | Daglow et al. |

(56) References Cited

U.S. PATENT DOCUMENTS

| | | | |
|---|---|---|---|
| 7,783,359 B2 | 8/2010 | Meadows | |
| 7,787,945 B2 | 8/2010 | Greene | |
| 7,792,590 B1 | 9/2010 | Pianca et al. | |
| 7,809,446 B2 | 10/2010 | Meadows | |
| 7,815,651 B2 | 10/2010 | Skakoon et al. | |
| 7,833,231 B2 | 11/2010 | Skakoon et al. | |
| 7,833,253 B2 | 11/2010 | Ralph et al. | |
| 7,949,395 B2 | 5/2011 | Kuzma | |
| 7,949,410 B2 | 5/2011 | Rodriguez | |
| 7,974,706 B2 | 7/2011 | Moffitt et al. | |
| 7,981,119 B2 | 7/2011 | Lando et al. | |
| 8,024,045 B2 | 9/2011 | Carlton et al. | |
| 8,043,304 B2 | 10/2011 | Barker | |
| 8,137,362 B2 | 3/2012 | Malinowski | |
| 8,175,710 B2 | 5/2012 | He | |
| 8,224,450 B2 | 7/2012 | Brase | |
| 8,271,094 B1 | 9/2012 | Moffitt et al. | |
| 8,295,944 B2 | 10/2012 | Howard et al. | |
| 8,313,453 B2 | 11/2012 | Carbunaru et al. | |
| 8,364,278 B2 | 1/2013 | Pianca et al. | |
| 8,391,985 B2 | 3/2013 | McDonald | |
| 8,397,732 B2 | 3/2013 | Singhal et al. | |
| 8,425,534 B2 | 4/2013 | Barker | |
| 8,473,061 B2 | 6/2013 | Moffitt et al. | |
| 8,571,664 B2 | 10/2013 | Anderson et al. | |
| 8,571,665 B2 | 10/2013 | Moffitt et al. | |
| 8,688,235 B1 | 4/2014 | Pianca et al. | |
| 8,731,686 B2 | 5/2014 | Lane et al. | |
| 8,764,767 B2 | 7/2014 | Barker | |
| 8,792,993 B2 | 7/2014 | Pianca et al. | |
| 8,812,133 B2 | 8/2014 | Funderburk | |
| 9,043,000 B2 | 5/2015 | Lane et al. | |
| 9,050,191 B2 | 6/2015 | Funderburk | |
| 9,084,901 B2 | 7/2015 | Wahlstrand | |
| 9,101,756 B1 | 8/2015 | Pianca et al. | |
| 9,468,751 B2 | 10/2016 | Bonde | |
| 9,474,896 B2 | 10/2016 | Lopez | |
| 9,492,660 B2 | 11/2016 | Mouchawar et al. | |
| 9,604,052 B2 | 3/2017 | Behymer et al. | |
| 9,610,437 B2 | 4/2017 | Okun et al. | |
| 10,232,169 B2 | 3/2019 | Govea et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0052610 A1 | 5/2002 | Skakoon et al. | |
| 2002/0072770 A1 | 6/2002 | Pless | |
| 2002/0077670 A1 | 6/2002 | Archer et al. | |
| 2002/0099412 A1 | 7/2002 | Fischell et al. | |
| 2002/0156372 A1 | 10/2002 | Skakoon et al. | |
| 2002/0169485 A1 | 11/2002 | Pless et al. | |
| 2003/0028199 A1 | 2/2003 | Ghahremani et al. | |
| 2003/0083724 A1 | 5/2003 | Jog et al. | |
| 2003/0088274 A1 | 5/2003 | Gliner et al. | |
| 2003/0088303 A1 | 5/2003 | Goode | |
| 2004/0034367 A1 | 2/2004 | Malinowski | |
| 2004/0122446 A1 | 6/2004 | Solar | |
| 2004/0153129 A1 | 8/2004 | Pless et al. | |
| 2004/0176673 A1 | 9/2004 | Wahlstrand et al. | |
| 2005/0003268 A1 | 1/2005 | Scott et al. | |
| 2005/0004618 A1 | 1/2005 | Scott et al. | |
| 2005/0010261 A1 | 1/2005 | Luders et al. | |
| 2005/0015128 A1 | 1/2005 | Rezai et al. | |
| 2005/0049646 A1 | 3/2005 | Luders et al. | |
| 2005/0070458 A1 | 3/2005 | John | |
| 2005/0075679 A1 | 4/2005 | Gliner et al. | |
| 2005/0075680 A1 | 4/2005 | Lowry et al. | |
| 2005/0092707 A1 | 5/2005 | Chantalat | |
| 2005/0107753 A1 | 5/2005 | Rezai et al. | |
| 2005/0182420 A1* | 8/2005 | Schulte | A61N 1/0539 606/130 |
| 2005/0182421 A1 | 8/2005 | Schulte et al. | |
| 2005/0182422 A1 | 8/2005 | Schulte et al. | |
| 2005/0182423 A1 | 8/2005 | Schulte et al. | |
| 2005/0182424 A1 | 8/2005 | Schulte et al. | |
| 2005/0182425 A1 | 8/2005 | Schulte et al. | |
| 2005/0182464 A1 | 8/2005 | Schulte et al. | |
| 2005/0222641 A1 | 10/2005 | Pless | |
| 2005/0228249 A1 | 10/2005 | Boling | |
| 2006/0129204 A1 | 6/2006 | Pless et al. | |
| 2006/0190054 A1 | 8/2006 | Malinowski et al. | |
| 2006/0190055 A1 | 8/2006 | Malinowski et al. | |
| 2006/0212093 A1 | 9/2006 | Pless et al. | |
| 2006/0224216 A1 | 10/2006 | Pless et al. | |
| 2006/0229686 A1 | 10/2006 | Giftakis et al. | |
| 2006/0247684 A1 | 11/2006 | Halperin et al. | |
| 2007/0106143 A1 | 5/2007 | Flaherty | |
| 2007/0150036 A1 | 6/2007 | Anderson | |
| 2007/0173844 A1 | 7/2007 | Ralph et al. | |
| 2007/0208352 A1 | 9/2007 | Henderson et al. | |
| 2007/0225773 A1 | 9/2007 | Shen et al. | |
| 2007/0233158 A1 | 10/2007 | Rodriguez | |
| 2007/0265683 A1 | 11/2007 | Ehrlich | |
| 2008/0071313 A1 | 3/2008 | Stevenson et al. | |
| 2008/0100061 A1 | 5/2008 | Sage et al. | |
| 2008/0172068 A1 | 7/2008 | Adams et al. | |
| 2008/0183220 A1* | 7/2008 | Glazer | A61B 17/686 606/303 |
| 2008/0243219 A1 | 10/2008 | Malinowski et al. | |
| 2008/0275466 A1 | 11/2008 | Skakoon | |
| 2009/0112327 A1 | 4/2009 | Lane et al. | |
| 2009/0118804 A1 | 5/2009 | Moffitt et al. | |
| 2009/0157157 A1 | 6/2009 | Schorn et al. | |
| 2009/0182351 A1 | 7/2009 | Malinowski et al. | |
| 2009/0187149 A1 | 7/2009 | Nelson | |
| 2009/0187222 A1 | 7/2009 | Barker | |
| 2009/0202899 A1 | 8/2009 | Pyszczek | |
| 2009/0276021 A1 | 11/2009 | Meadows et al. | |
| 2010/0023020 A1 | 1/2010 | Barker et al. | |
| 2010/0023100 A1 | 1/2010 | Barker | |
| 2010/0076535 A1 | 3/2010 | Pianca et al. | |
| 2010/0114249 A1 | 5/2010 | Wahlstrand et al. | |
| 2010/0145357 A1 | 6/2010 | Lane et al. | |
| 2010/0268298 A1 | 10/2010 | Moffitt et al. | |
| 2010/0280585 A1 | 11/2010 | Appenrodt et al. | |
| 2010/0312193 A1 | 12/2010 | Stratton et al. | |
| 2011/0004267 A1 | 1/2011 | Meadows | |
| 2011/0005069 A1 | 1/2011 | Pianca | |
| 2011/0054563 A1 | 3/2011 | Janzig et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | Digiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | Digiore et al. | |
| 2012/0203321 A1 | 8/2012 | Moffitt et al. | |
| 2012/0316615 A1 | 12/2012 | Digiore et al. | |
| 2012/0316628 A1 | 12/2012 | Lopez | |
| 2013/0006410 A1 | 1/2013 | Gentile et al. | |
| 2013/0066430 A1 | 3/2013 | Funderburk | |
| 2013/0066431 A1 | 3/2013 | Funderburk | |
| 2013/0105071 A1 | 5/2013 | Digiore et al. | |
| 2013/0197424 A1 | 8/2013 | Bedenbaugh | |
| 2013/0197602 A1 | 8/2013 | Pianca et al. | |
| 2013/0304216 A1 | 11/2013 | Paspa et al. | |
| 2014/0039587 A1 | 2/2014 | Romero | |
| 2014/0155909 A1* | 6/2014 | Bonde | A61M 25/04 606/130 |
| 2014/0257325 A1 | 9/2014 | Chavez et al. | |
| 2014/0353001 A1 | 12/2014 | Romero et al. | |
| 2014/0358207 A1 | 12/2014 | Romero | |
| 2014/0358208 A1 | 12/2014 | Howard et al. | |
| 2014/0358209 A1 | 12/2014 | Romero et al. | |
| 2014/0358210 A1 | 12/2014 | Howard et al. | |
| 2015/0018915 A1 | 1/2015 | Leven | |
| 2015/0045864 A1 | 2/2015 | Howard | |
| 2015/0051681 A1 | 2/2015 | Hershey | |

(56) References Cited

U.S. PATENT DOCUMENTS

| 2015/0066120 | A1 | 3/2015 | Govea |
| 2015/0151113 | A1 | 6/2015 | Govea et al. |
| 2016/0228692 | A1 | 8/2016 | Steinke et al. |
| 2019/0060637 | A1* | 2/2019 | Duijsens ............... A61M 25/04 |
| 2019/0143125 | A1 | 5/2019 | Funderburk et al. |

FOREIGN PATENT DOCUMENTS

| WO | 1998008554 | 3/1998 |
| WO | 1999055408 | 11/1999 |
| WO | 2000013743 | 3/2000 |
| WO | 20020045795 | 6/2002 |
| WO | 2003026738 | 4/2003 |
| WO | 20030028521 | 4/2003 |
| WO | 20040084749 | 10/2004 |
| WO | 2004105640 | 12/2004 |
| WO | 2005079903 | 9/2005 |
| WO | 2006031317 | 3/2006 |
| WO | 2008054691 | 5/2008 |
| WO | 2008054699 | 5/2008 |
| WO | 2008107815 | 9/2008 |
| WO | 2008107822 | 9/2008 |
| WO | 2008134509 | 11/2008 |
| WO | 2009055746 | 4/2009 |

OTHER PUBLICATIONS

Roberts DW, Hartov A. Kennedy FE, Miga MI, Paulsen KD: Intraoperative brain shift and deformation: A quantitative analysis of cortical displacement in 28 cases. Neurosurgery 43:749-760, 1998.

Dickhaus H., Ganser KA, Stuabert A., Bonsanto MM, Wirtz CR, Tronnier VM, Kunze S: Quantification of brain shift effects by MR-imaging. Engineering in Medicine and Biology Society vol. 2: 491-494, 1997.

Nimsky C., Gansland O., Cerny S., Hastreiter P, Greiner G., Fahlbusch R.: Quantification of, visualization of, and compensation for brain shift using intraoperative magnetic resonance imaging. Neurosurgery 47, 1070-1080, 2000.

Winkler D., Tittgemeyer M., Schwartz J., Preul C., Strecker K., Meixensberger J.: The first evaluation of brain shift during functional neurosurgery by deformation field analysis. Journal of Neurology, Neurosurgery, and Psychiatry 76(8): 1161-3, 2005.

Axelsson, Stefan et al., Longitudinal cephalometric standards for the neurocranium in Norwegians from 6 to 21 years of age, European Journal of Orthodontics, vol. 25 (2003) pp. 185-198.

International Search Report and Written Opinion for PCT Application No. PCT/US2019/020670 dated May 22, 2019.

* cited by examiner

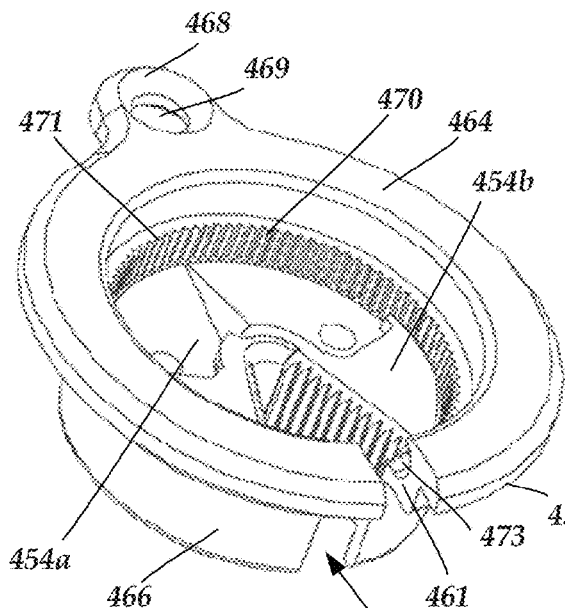
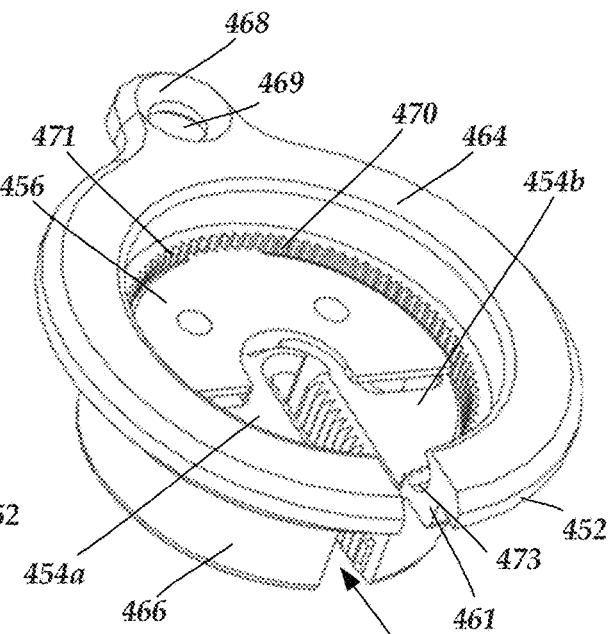
Fig. 7A  Fig. 7B
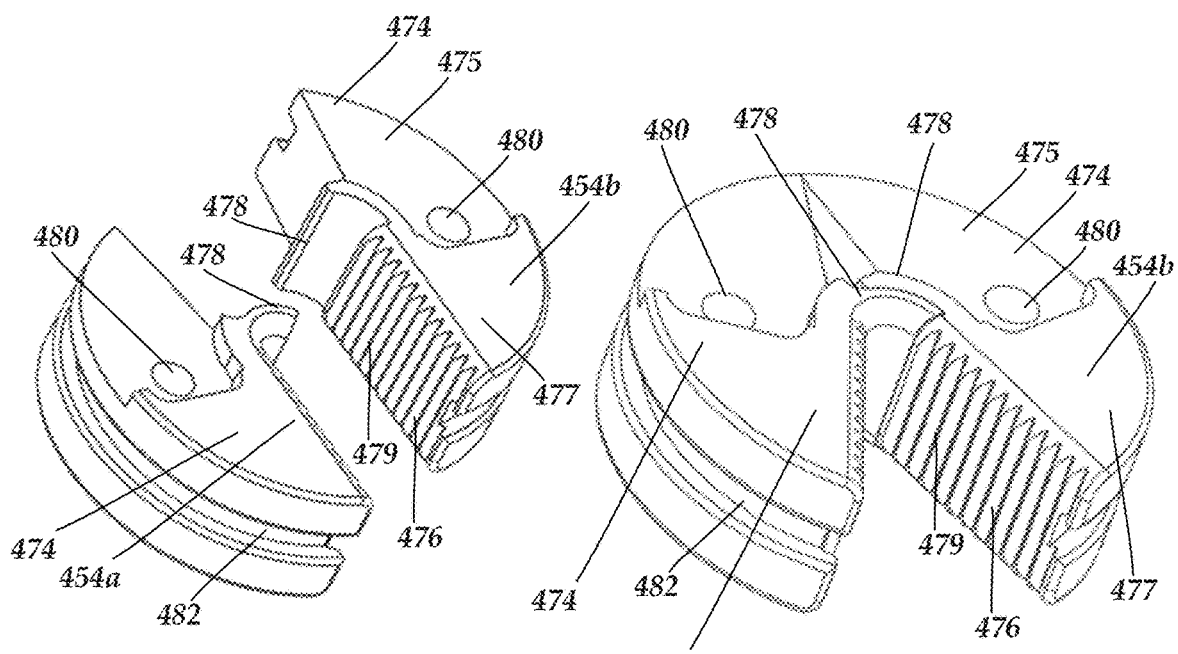
Fig. 8A  Fig. 8B

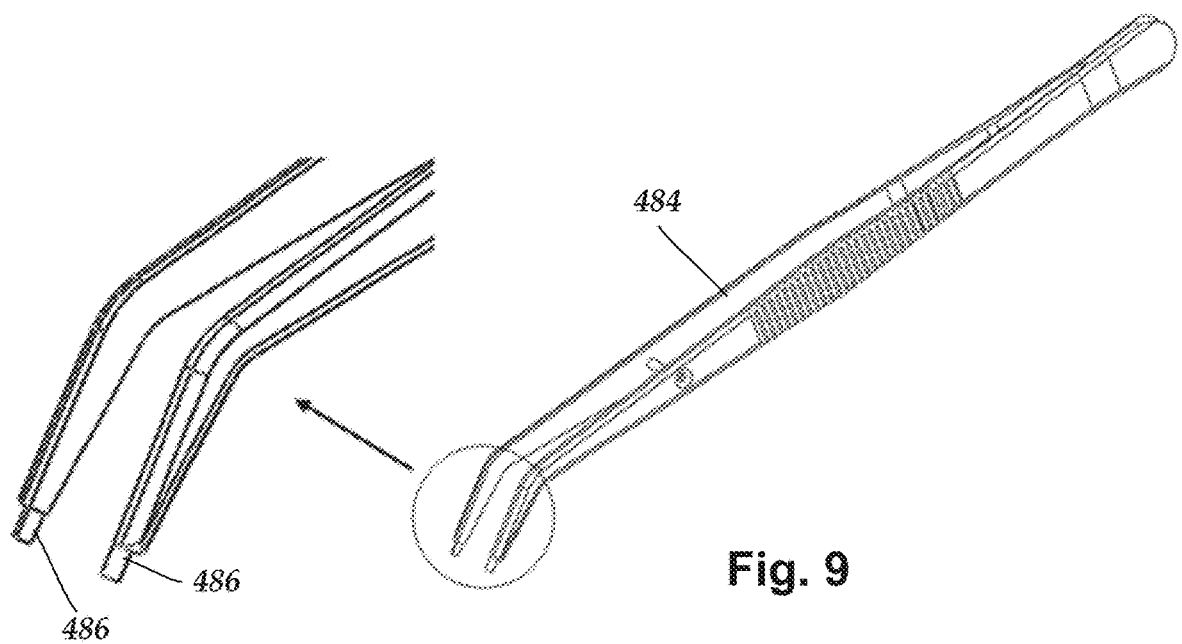
Fig. 9
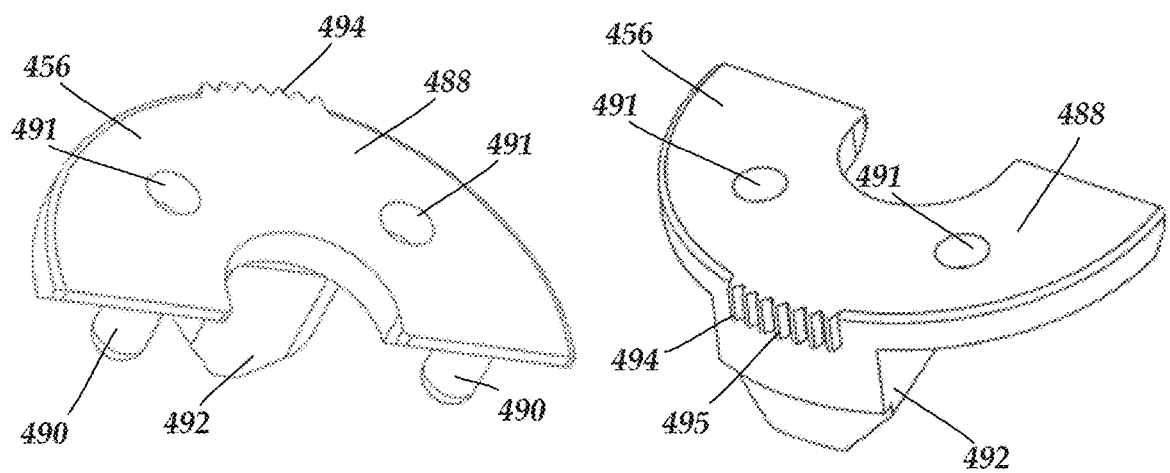
Fig. 10A
Fig. 10B
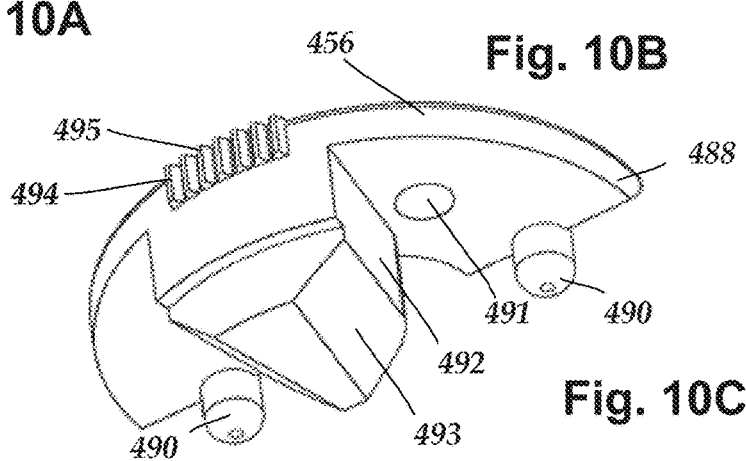
Fig. 10C

BURR HOLE PLUGS FOR ELECTRICAL STIMULATION SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/641,180, filed Mar. 9, 2018, which is incorporated herein by reference.

FIELD

The present disclosure is directed to the area of implantable electrical stimulation systems and methods of making and using the systems. The present disclosure is also directed to burr hole plugs and implantable electrical stimulation systems including the burr hole plugs, as well as methods of making and using the burr hole plugs and electrical stimulation systems.

BACKGROUND

Implantable electrical stimulation systems have proven therapeutic in a variety of diseases and disorders. For example, stimulation of the brain, such as deep brain stimulation, can be used to treat a variety of diseases or disorders, and spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the brain, nerves, or other tissue to be stimulated. The pulse generator in the control module generates electrical pulses that are delivered by the electrodes to body tissue.

BRIEF SUMMARY

In some aspects, a burr hole plug includes a base defining a burr hole aperture and having a flange configured to rest on the skull of a patient and a sidewall configured to extend into a burr hole in the skull of the patient, wherein the flange defines at least one fastener opening; and a flexible cover configured to be disposed entirely over, and coupled to, the base, wherein the flexible cover includes a skirt configured to fit around an outer perimeter of the base and a rim that fits inside the sidewall of the base, wherein between the skirt and the rim is an inset region having a shape corresponding to a shape of the flange of the base.

In some aspects, a burr hole plug includes a base defining a burr hole aperture and having a flange configured to rest on the skull of a patient, a sidewall configured to extend into a burr hole in the skull of the patient, and an engagement region extending around the sidewall; two lead retention members configured for placement within the base, each of the lead retention members including a lead engagement surface to engage and hold a lead between the two lead retention members; a locking member configured for placement within the base and for engaging the two lead retention members to lock the two lead retention members in a lead engagement position and for engaging the engagement region of the base to prevent rotation of the two lead retention members within the base; and a cover configured to be disposed over, and coupled to, the base.

The components and features of the burr hole plugs described hereinabove can be combined with each other.

In some aspects, each of the lead retention members includes a receiving opening and the locking member includes two pins configured for insertion in the receiving openings of the two lead retention members to lock the two lead retention members in the lead engagement position. In some aspects, the locking member includes a wedge element configured for insertion between the two lead retention members to separate the two lead retention members and drive the lead engagement surfaces of the two lead retention members toward each other. In some aspects, the engagement region of the base includes a plurality of teeth and the locking member includes a retention element having a plurality of teeth to engage the teeth of the engagement region of the base to prevent rotation of the locking element and the two lead retention members within the base.

In some aspects, the base includes a ridge around the sidewall and each of the lead retention members includes a circumferential groove that is configured to receive the ridge of the base. In some aspects, each of the lead retention members includes a curved rotation limiting element, wherein, absent the locking member, the two lead retention members are configured to swivel within the base limited, at least in part, by the curved rotation limiting elements. In some aspects, the lead engagement surface of each of the two lead retention members includes a plurality of vertical teeth for securely holding the lead.

In some aspects, the cover includes an opening for exit of the lead. In some aspects, the cover includes a skirt configured to fit around an outer perimeter of the base and a rim that fits inside the sidewall of the base.

In some aspects, the base defines a gap for receiving at least a portion of the lead. In some aspects, the burr hole plug further includes a fastener and a fastener holder for safely holding the fastener prior to removal for insertion in the skull to fasten the base to the skull. In some aspects, the fastener holder includes a plurality of fingers configured for compression when inserted in the base to retain the fastener holder within the base. In some aspects, the cover is made of silicone. In some aspects, the base includes a single fastener opening for receiving a single fastener to fasten the base to the skull.

In some aspects, a burr hole plug includes a base defining a burr hole aperture and having a flange configured to rest on the skull of a patient and a sidewall configured to extend into a burr hole in the skull of the patient, wherein the flange defines at least one fastener opening; and a flexible cover configured to be disposed entirely over, and coupled to, the base, wherein the flexible cover includes a skirt configured to fit around an outer perimeter of the base and a rim that fits inside the sidewall of the base, wherein between the skirt and the rim is an inset region having a shape corresponding to a shape of the flange of the base.

In some aspects, the cover is made of silicone. In some aspects, the cover includes an opening for exit of the lead.

In some aspects, a system for electrical stimulation includes any of the burr hole plugs described above and a lead configured for insertion into the skull and for engagement with the burr hole plug.

In some aspects, a method of using any of the burr hole plugs described above includes inserting the base into a burr hole in a skull of a patient; inserting the two lead retention members into the base; inserting the locking member into the base and engaging and locking the two lead retention members relative to each other; and disposing the cover over the base.

In some aspects, inserting the base includes sliding the base over a portion of the lead. In some aspects, inserting the locking member includes separating the two lead retention members using a wedge element of the locking member and locking the two lead retention members by inserting pins of the locking member into corresponding receiving openings in the two lead retention members. In some aspects, inserting the two lead retention members includes fitting a ridge defined in the sidewall of the base into a circumferential groove in each of the lead retention members. In some aspects, inserting the two lead retention members includes rotating the two lead retention members to position a lead extending through the base between the lead engagement surfaces of the two lead retention members.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is a perspective view of one embodiment of the base and lead retention elements of the burr hole plug of FIG. 4;

FIG. 7B is a perspective view of one embodiment of the base, lead retention elements, and locking element of the burr hole plug of FIG. 4;

FIG. 8A is a perspective view of one embodiment of the lead retention elements of the burr hole plug of FIG. 4;

FIG. 8B is a perspective view of the lead retention elements of the burr hole plug of FIG. 4 engaged with each other;

FIG. 9 is a perspective view and detail view of a tool for use with the lead retention element of FIGS. 8A and 8B and the locking member of FIGS. 7B, 10A, 10B, and 10C;

FIG. 10A is a perspective top-front view of one embodiment of a locking member of the burr hole plug of FIG. 4;

FIG. 10B is a perspective top-back view of one embodiment of a locking member of the burr hole plug of FIG. 4;

FIG. 10C is a perspective bottom view of one embodiment of a locking member of the burr hole plug of FIG. 4;

DETAILED DESCRIPTION

The present disclosure is directed to the area of implantable electrical stimulation systems and methods of making and using the systems. The present disclosure is also directed to burr hole plugs and implantable electrical stimulation systems including the burr hole plugs, as well as methods of making and using the burr hole plugs and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that such leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
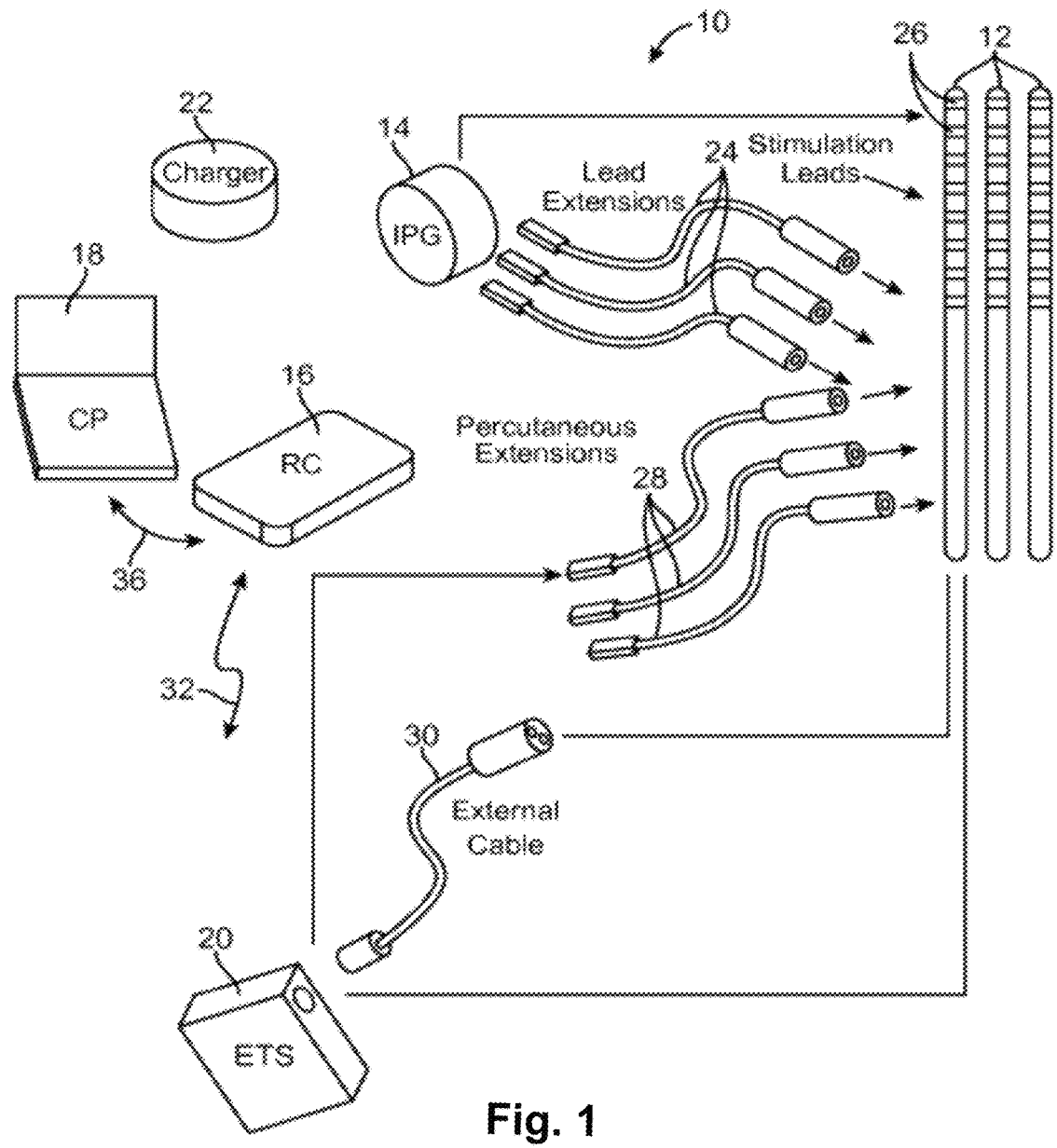
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
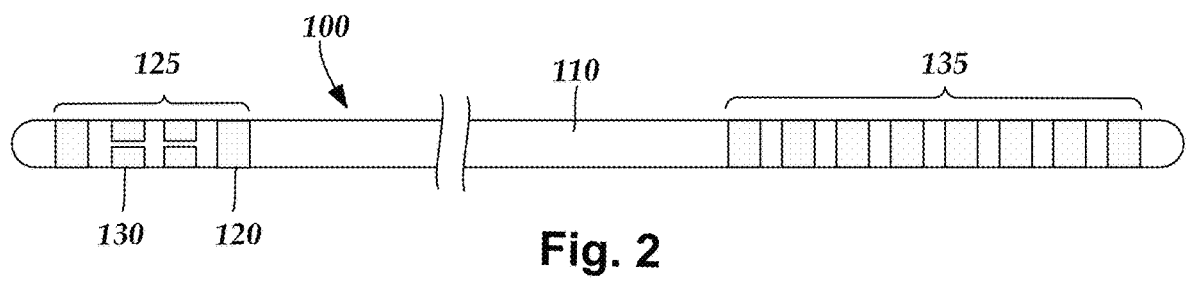
FIG. 2 is a schematic side view of one embodiment of an electrical stimulation lead.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes. It will be understood that the leads could include any suitable number of electrodes. The leads can include ring electrode, a distal-tip electrode, or one or more segmented electrodes, or any combination thereof. Additionally, the term "elongated member" used herein includes leads (e.g., percutaneous, paddle, cuff, or the like), as well as intermediary devices (e.g., lead extensions, adaptors, splitters, or the like).

FIG. 2 illustrates one embodiment of a lead 100 with electrodes 125 disposed at least partially about a circumference of the lead 100 along a distal end portion of the lead and terminals 135 disposed along a proximal end portion of the lead. The lead 100 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of a stylet (not shown). The lead 100 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 100, advance the lead 100, retract the lead 100, or rotate the lead 100.

The lead 100 for deep brain stimulation can include stimulation electrodes, recording electrodes, or both. In at least some embodiments, the lead 100 is rotatable so that the stimulation electrodes can be aligned with the target neurons after the neurons have been located using the recording electrodes.

Stimulation electrodes may be disposed on the circumference of the lead 100 to stimulate the target neurons. Stimulation electrodes may be ring-shaped so that current projects from each electrode equally in every direction from the position of the electrode along a length of the lead 100. In the embodiment of FIG. 2, two of the electrodes 125 are ring electrodes 120. Ring electrodes 120 typically do not enable stimulus current to be directed from only a limited angular range around of the lead. Segmented electrodes 130, however, can be used to direct stimulus current to a selected angular range around the lead 100. When segmented electrodes 130 are used in conjunction with an implantable pulse generator that delivers constant current stimulus, current steering can be achieved to more precisely deliver the stimulus to a position around an axis of the lead (i.e., radial positioning around the axis of the lead 100). To achieve current steering, segmented electrodes 130 can be utilized in addition to, or as an alternative to, ring electrodes 120.

As described above, the lead 100 includes a lead body 110, terminals 135, and one or more ring electrodes 120 and one or more sets of segmented electrodes 130 (or any other combination of electrodes). The lead body 100 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used (ON) or unused (OFF). When the electrode is used, the electrode can be used as an anode or cathode and carry anodic or cathodic current. In some instances, an electrode might be an anode for a period of time and a cathode for a period of time.

As described above, deep brain stimulation leads and other leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent applications Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
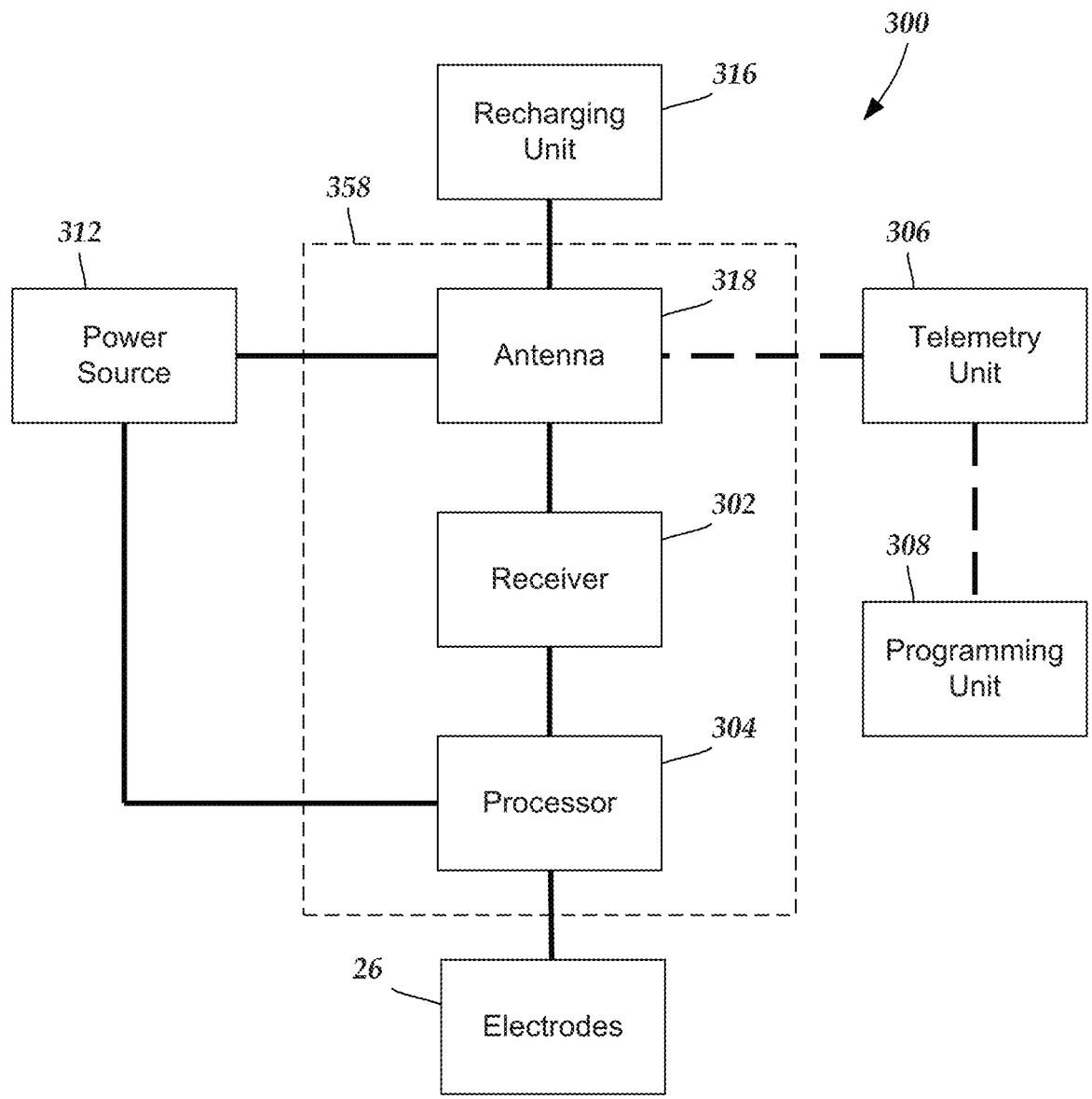
FIG. 3 is a schematic overview of one embodiment of components of a stimulation system, including an electronic subassembly disposed within a control module.

FIG. 3 is a schematic overview of one embodiment of components of an electrical stimulation system 300 including an electronic subassembly 358 disposed within a control module. The electronic subassembly 358 may include one or more components of the IPG. It will be understood that the electrical stimulation system can include more, fewer, or different components and can have a variety of different configurations including those configurations disclosed in the stimulator references cited herein.

Some of the components (for example, a power source 312, one or more antennas 318, a receiver 302, and a processor 304) of the electrical stimulation system can be positioned on one or more circuit boards or similar carriers within a sealed electronics housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. In at least some embodiments, the antenna 318 (or the secondary antenna) is implemented using the auxiliary electrically-conductive conductor. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above. The electronic subassembly 358 and, optionally, the power source 312 can be disposed within a control module (e.g., the IPG 14 or the ETS 20 of FIG. 1).

In one embodiment, electrical stimulation signals are emitted by the electrodes (e.g., electrode array 26 in FIG. 1) to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Various processors can be used and may be an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit 308 is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

In at least some instances of electrical stimulation of the brain, when a lead is implanted into the brain of a patient, the lead is inserted through a burr hole in the skull of the patient. The lead extends out of the burr hole and is coupled to a control module implanted elsewhere, for example, in the torso of the patient. A burr hole plug is provided in the burr hole to cover the opening through the skull, to protect the lead exiting the skull, and to firmly hold the lead in place to prevent or reduce lead migration within the brain.

Conventional burr hole plugs may present challenges with respect to a number of factors including lead retention, softness, flexibility, and profile. Many conventional burr hole plugs may be considered unduly large, tall, high-profile, or unappealing. Many conventional burr hole plugs may not adequately hold the lead in place and prevent movement or shifting which may alter the position of the lead within the brain of the patient. Some conventional burr hole plugs force the lead to bend at a right angle at the exit without any protection which makes the lead vulnerable to fracture or short circuiting. During placement of many conventional burr hole plugs, the exiting lead may move from its precise target site in the brain. After placement of many conventional burr hole plugs, even a slight bending or deflection of the lead may cause repositioning of the lead. Also, a lead, not secured properly, may migrate over time and could require additional surgical procedures to correct. In addition, sharp edges of a burr hole plug base or cover can contribute to skin erosion, which can result in open lesions and eventually infection.

Figure 4:
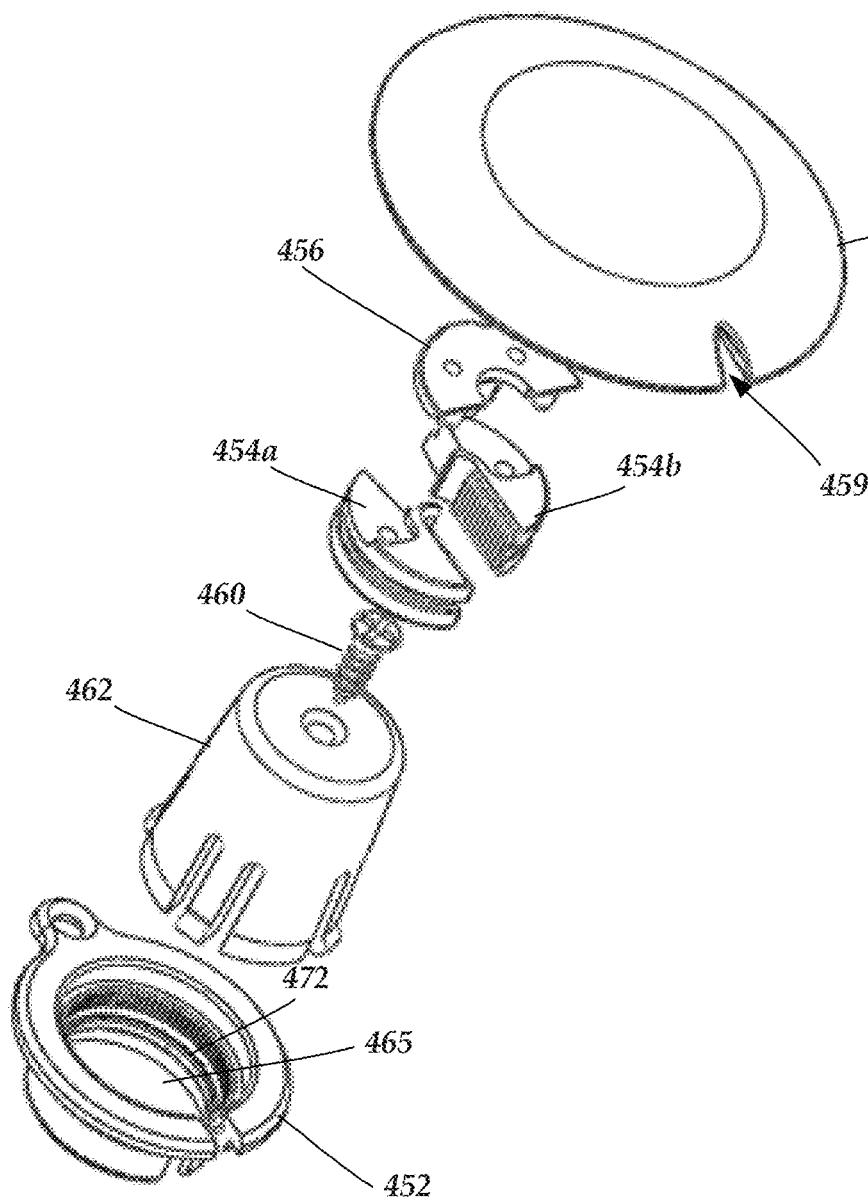
FIG. 4 is an exploded perspective view of components of one embodiment of a burr hole plug.
Figures 5A, 5B:
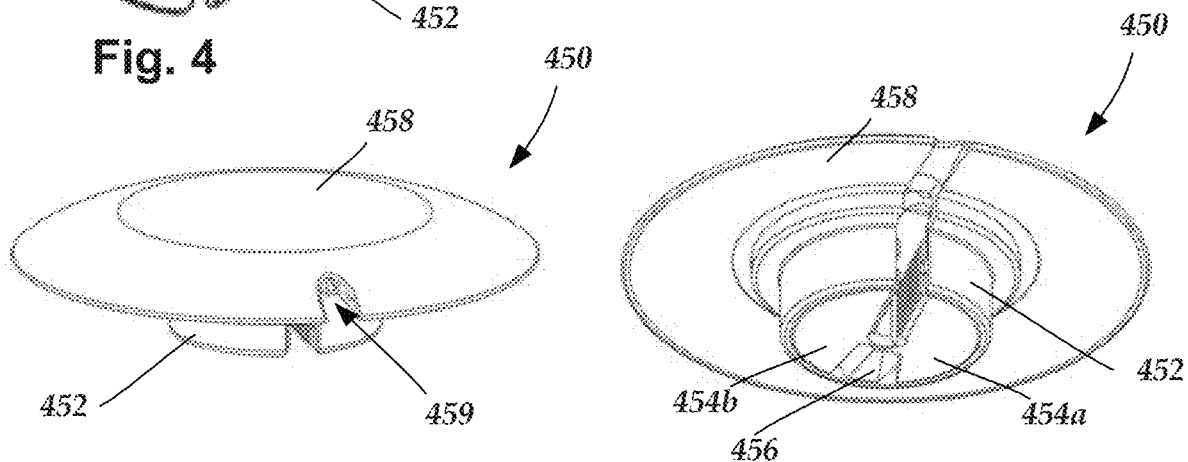
FIG. 5A is a perspective top view of the assembled burr hole plug of FIG. 4.
FIG. 5B is a perspective bottom view of the assembled burr hole plug of FIG. 4.

A burr hole plug can be designed to address one or more of these concerns. FIG. 4 illustrates, in an exploded view, one embodiment of a burr hole plug 450 that includes a base 452, two lead retention members 454a, 454b, a locking member 456, a cover 458, a fastener 460, and an optional fastener holder 462. FIGS. 5A and 5B illustrate the assembled burr hole plug 450 (which does not include the optional fastener holder 462). In at least some embodiments, the burr hole plug 450 can have a low profile of 3 mm or less above the skull. In at least some embodiments, the base 452 and cap 458 of the burr hole plug may be smooth and flexible and follow the curvature of the skull to reduce or prevent skin erosion and infection. In at least some embodiments, only a single fastener 460 is used for attachment to the skill. In at least some embodiments, the burr hole plug includes only a single exit 459 for the lead to reduce the edges of the burr hole plug. The single exit 459 can be rotated around the skull prior to fastening the base 452 and placing the cover 458 to a desired exit direction or position.

Figure 6A:
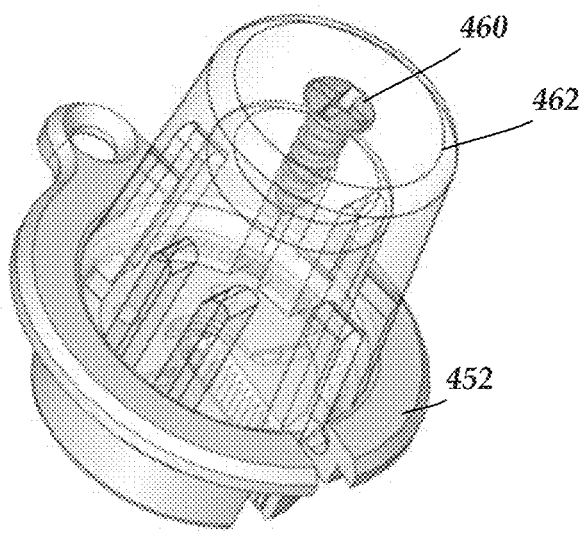
FIG. 6A is a perspective side view of one embodiment of some of the components of the burr hole plug of FIG. 4 including a fastener holder.
Figure 6B:
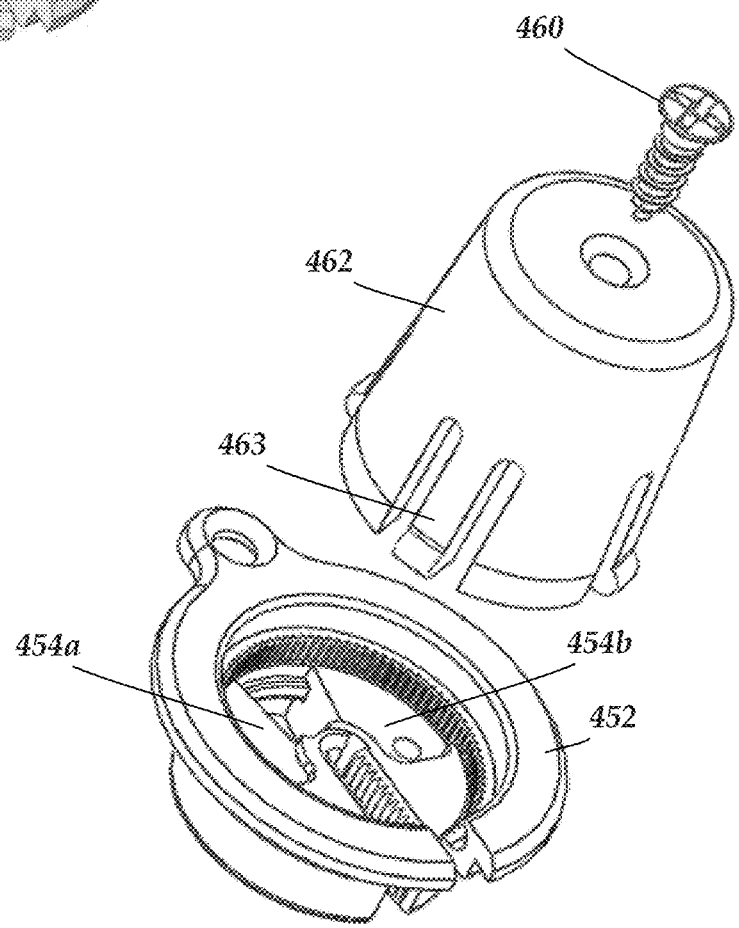
FIG. 6B is a perspective exploded view of one embodiment of some of the components of the burr hole plug of FIG. 4 including a fastener holder.

FIG. 6A illustrates one embodiment of components of the burr hole plug 450 as packaged prior to use. FIG. 6B illustrates the removal of the optional fastener holder 462 and fastener 460. The fastener holder 462 is primarily provided to avoid misplacing the fastener 460 and may also be provided to hold components such as the two lead retention members 454a, 454b and the locking member 456 in the base 452 prior to use. In this manner, the small components of the burr hole plug 450 are not misplaced or lost. The fastener holder 462 fits into the base 452, as illustrated in FIG. 6A and includes fingers 463 that can be engaged or compressed within the base 452 to retain the fastener holder in the base. The fastener 460, such as a screw, can be removed from the fastener holder 462 using a tool, such as a screw driver. The fastener holder 462 can be made of any suitable material including, but not limited to, rigid plastics, thermoplastics, metal, or any combination thereof and, in some embodiments, may be transparent or translucent.

The base 452 fits within a burr hole made in the skull of a patient. FIGS. 6B, 7A, and 7B illustrate one embodiment of a base 452 that has a flange 464 which may rest on the skull and a sidewall 466 that extends into the burr hole and defines a burr hole aperture 465 (FIG. 4). Optionally, the base 452 includes a gap 467 for receiving a portion of the lead as the base 452 is slid onto or into the burr hole after the lead has been implanted, if desired. The flange 464 includes one or more tabs 468, each tab 468 having an opening 469 to receive the fastener 460 to secure the base 452 to the skull of the patient. It will be understood that other fastening arrangements can also be used.

The base 452 can be made of any suitable material including, but not limited to, plastic, metal, ceramic, or any combination thereof. In some embodiments, at least the flange 464 has some flexibility to conform with the shape of the skull on which it rests. In at least some embodiments, the sidewall 466 forms a friction or compression fit with the burr hole in which it is placed.

The interior portion of the sidewall 466 of the base 452 includes an engagement region 470 with vertical teeth 471 (e.g., alternating ridges and valleys). The teeth 471 of the engagement region 470 engage corresponding teeth on the locking member 456, as described below, to prevent or hinder the locking member 456 and lead retention members 454a, 454b from rotating within the base 452 after the locking member 456 is placed. The interior portion of the sidewall 466 of the base 452 may also include a bottom ridge 472 (FIG. 4) upon which the lead retention members 454a, 454b fit when placed in the base. The interior portion of the sidewall 466 of the base 452 may also include a shoulder 461 connecting the flange 464 to the remainder of the sidewall and arranged to fit, for example, in a countersunk portion of the burr hole. The shoulder 461 and flange 464 may define a detent 473 for receiving a ridge of the cover 458.

FIGS. 8A and 8B illustrate one embodiment of the two lead retention members 454a, 454b. The lead retention members 454a, 454b can be made of any suitable material including, but not limited to, plastic, ceramic, or metal or any combination thereof. In at least some embodiments, each lead retention member 454a, 454b has a form of less than half of a cylinder having an outer diameter equal to, or slightly less than, an inner diameter of the base 452. In the illustrated embodiment, each lead retention member 454a, 454b has a main body 474, a lead engagement surface 476, an optional curved rotation limiting element 478, a receiving opening 480, and a circumferential groove 482.

In at least some embodiments, the lead retention member 454a, 454b is positioned in the base 452, the ridge 472 (FIG. 4) of the base fits into the circumferential groove 482 to hold the lead retention members within the base. In at least some embodiments, prior to insertion of the locking member 456, the lead retention members 454a, 454b can rotate within the base 452. The lead retention members 454a, 454b can also swivel with respect to each other. FIG. 7A illustrates the lead retention members 454a, 454b disposed within the base 452 prior to the insertion of the locking member 456.

The separation between the lead engagement surfaces 476 of the two lead retention members 454a, 454b is constrained by either engagement of the main bodies 474 or the curved rotation limiting elements 478 or a combination of both, as illustrated in FIG. 8B. In at least some embodiments, a portion 475 of the main bodies 474 of the lead retention members 454a, 454b is inset relative to a remaining portion 477 to receive the locking member 456. The lead engagement surfaces 476 of the lead retention members 454a, 454b preferably include surface elements, such as the illustrated vertical teeth 479, that can engage and securely hold a lead in place between the two lead engagement surfaces and prevent or reduce slippage of the lead relative to the burr hole plug 450. Examples of other surface elements include, but are not limited to, roughened surfaces, horizontal teeth, diagonal or other non-vertical teeth, a pattern of peaked elements, or the like, or any combination thereof.

FIG. 9 illustrates one embodiment of a tool 484 that can be used to manipulate, rotate, and swivel the lead retention members 454a, 454b. Additionally or alternatively, the tool 484 can be used to manipulate or insert the locking member 456. In the illustrated embodiment of FIG. 9, the tool 484 is a pair of tweezers with small pins 486 on the tips that can fit within the receiving openings 480 of the lead retention members 454a, 454b and also in receiving openings 491 (FIG. 10A) in the locking member 456. In operation, the tool 484 can engage one or both of the lead retention members 454a, 454b, for example, with a pin 486 in the corresponding receiving opening 480, and then rotate or swivel one or both of the lead retention elements 454a, 454b.

FIGS. 10A-10C illustrate one embodiment of a locking member 456. The locking member 456 can be made of any suitable material including, but not limited to, plastic, metal, ceramic, or any combination thereof. In the illustrated embodiment, the locking member 456 includes a body 488, two pins 490, a wedge element 492, and a retention element 494.

The pins 490 extend from the body 488 and are configured to fit within the openings 480 in the lead retention members 454a, 454b. The wedge element 492 also fits between the two lead retention members 454a, 454b to separate, and properly position, the two lead retention members and drive the lead engagement surfaces 476 toward each other to grip the lead between the two lead engagement surfaces in a lead engagement position. The wedge element 492 optionally includes one or more sloped bottom surfaces 493 to facilitate inserting the wedge element 492 between the two lead retention members 454a, 454b and separating the two lead retention members from each other.

The retention element 494 includes teeth 495 for engaging the teeth 471 of the engagement region 470 of the base 452. This engagement between the teeth 495 of the retention element 494 and teeth 471 of the engagement region 470 prevents the locking member 456 and lead retention members 454a, 454b from rotating within the base 452 when the locking member 456 is inserted into the base 452. This arrangement facilitates maintaining the lead in the same position. FIG. 7B illustrates the lead retention members 454a, 454b and locking member 456 disposed within the base 452.

Figures 11A, 11B:
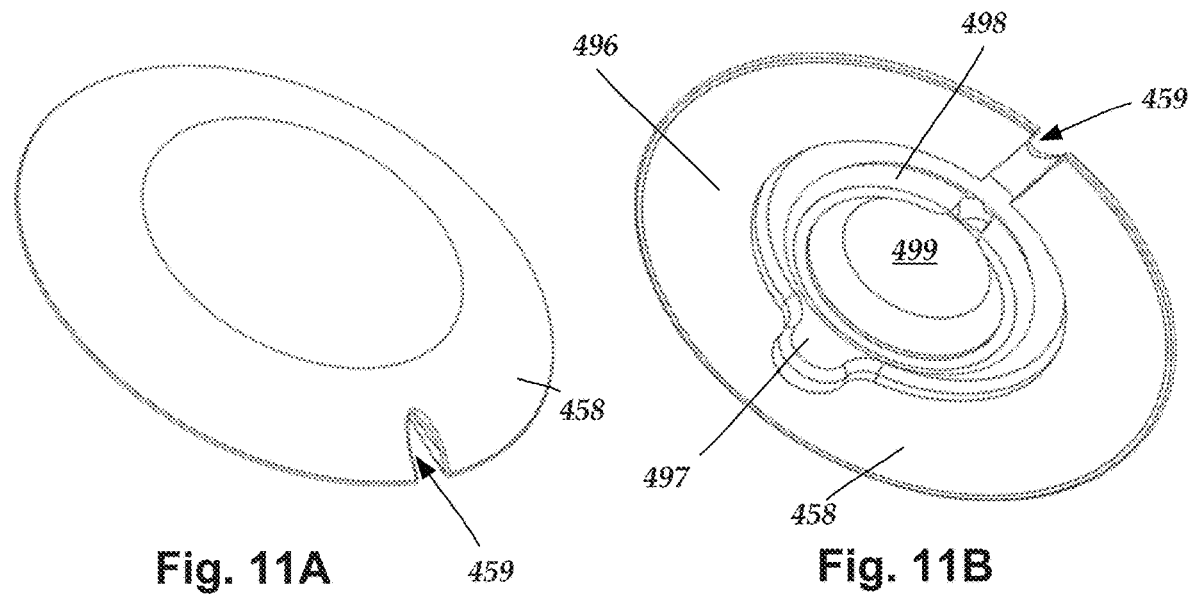
FIG. 11A is a perspective top view of one embodiment of a cover of the burr hole plug of FIG. 4.
FIG. 11B is a perspective bottom view of one embodiment of a cover of the burr hole plug of FIG. 4.
Figure 12:
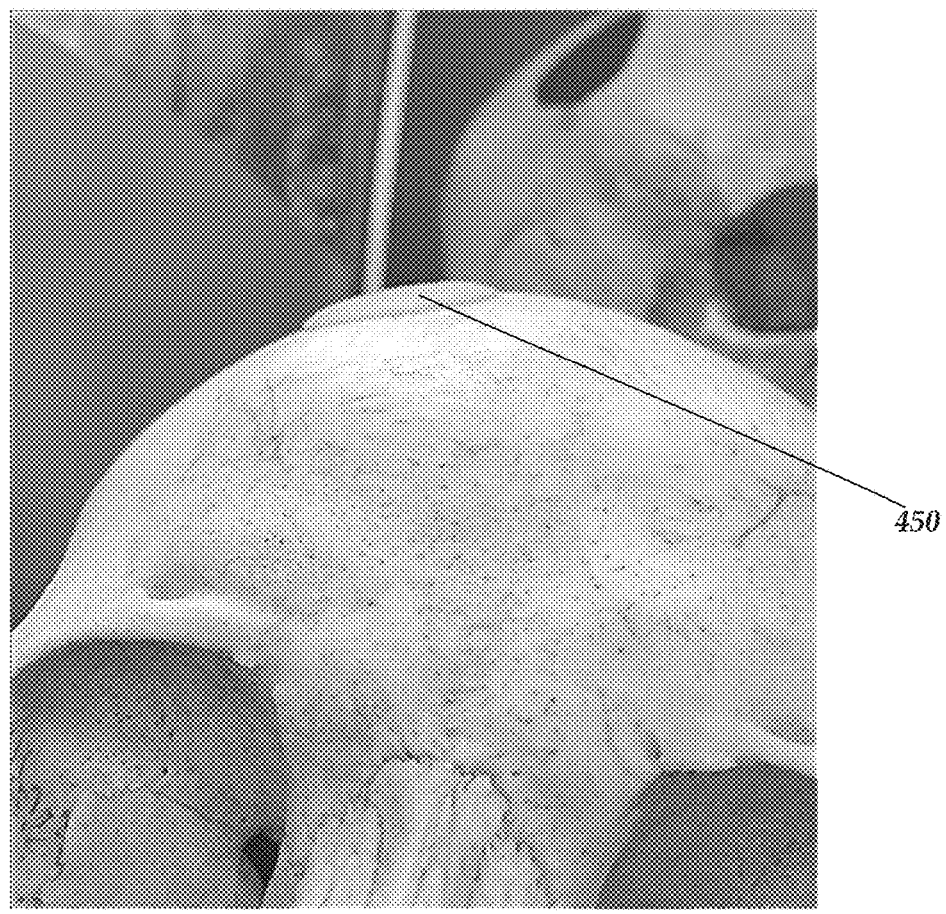
FIG. 12 is an image of a burr hole plug fixed in a skull.

FIGS. 11A and 11B illustrate the cover 458 which also defines an opening 459 for exit of the lead. The cover 458 is preferably made of a soft material such as silicone and preferably is smooth and flexible. Flexibility of the cover 458 may facilitate following the curvature of the skull of the patient and reduce tissue erosion and reduce the height of the burr hole plug, as illustrated in FIG. 12. In at least some embodiments, the cover 458 covers the entire base 452. In at least some embodiments, the cover 458 provides a gentle, tapering slope to reduce or prevent tissue erosion.

In at least some embodiments, the cover 458 may include a skirt 496 that fits around the outer perimeter of the base 452 including the tab 468 (see, e.g., FIGS. 7A-7B) to fit firmly on the base 452, a rim or ridge 498 that fits inside the sidewall 466, an inset region 497 between the skirt 496 and the rim corresponding to a shape of the flange 464 of the base 452, and a center region 499. In at least some embodiments, the rim 498 fits into a detent 473 formed by the sidewall 466 of the base 452 and may facilitate retention of the cover 458 on the base 452. In at least some embodiments, the insert region 464 allows the cover 458 and base 452 to have a low profile as the cover fits onto the base with relatively small increase in the extension of the burr hole plug above the skull relative to the base alone.

The above specification, examples and data provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A burr hole plug, comprising:
   a base defining a burr hole aperture and comprising a flange configured to rest on a skull of a patient, a sidewall configured to extend into a burr hole in the skull of the patient, and an engagement region extending around the sidewall;

two lead retention members configured for placement within the base, each of the two lead retention members comprising a lead engagement surface to engage and hold a lead between the two lead retention members;

a locking member configured for placement within the base and for engaging the two lead retention members to lock the two lead retention members in a lead engagement position and for engaging the engagement region of the base to prevent rotation of the two lead retention members within the base, wherein each of the two lead retention members comprises a receiving opening and the locking member comprises two pins configured for insertion in the receiving openings of the two lead retention members to lock the two lead retention members in the lead engagement position, wherein the locking member comprises a wedge element, spaced apart from the two pins, configured for insertion between the two lead retention members to separate the two lead retention members and drive the lead engagement surfaces of the two lead retention members toward each other; and a cover configured to be disposed over, and coupled to, the base.

2. The burr hole plug of claim 1, wherein the cover is configured to be disposed entirely over, and coupled to, the base, wherein the cover comprises a skirt configured to fit around an outer perimeter of the base and a rim that fits inside the sidewall of the base, wherein between the skirt and the rim is an inset region having a shape corresponding to a shape of the flange of the base.

3. The burr hole plug of claim 1, wherein the cover is made of silicone.

4. The burr hole plug of claim 1, wherein the cover comprises an opening for exit of the lead.

5. The burr hole plug of claim 1, wherein the engagement region of the base comprises a plurality of teeth and the locking member comprises a retention element having a plurality of teeth to engage the teeth of the engagement region of the base to prevent rotation of the locking element and the two lead retention members within the base.

6. The burr hole plug of claim 1, wherein the base comprises a ridge around the sidewall and each of the two lead retention members comprises a circumferential groove that is configured to receive the ridge of the base.

7. The burr hole plug of claim 1, wherein the lead engagement surface of each of the two lead retention members comprises a plurality of vertical teeth for securely holding the lead.

8. The burr hole plug of claim 1, wherein the base defines a gap for receiving at least a portion of the lead.

9. The burr hole plug of claim 1, further comprising a fastener and a fastener holder for safely holding the fastener for insertion in the skull to fasten the base to the skull.

10. The burr hole plug of claim 9, wherein the fastener holder comprises a plurality of fingers configured for compression when inserted in the base to retain the fastener holder within the base.

11. The burr hole plug of claim 1, wherein the base comprises a single fastener opening for receiving a single fastener to fasten the base to the skull.

12. A system for electrical stimulation, comprising:
the burr hole plug of claim 1, and
a lead configured for insertion into the skull and for engagement with the burr hole plug.

13. A method of using the burr hole plug of claim 1, the method comprising:
inserting the base into a burr hole in a skull of a patient;
inserting the two lead retention members into the base;
inserting the locking member into the base and engaging and locking the two lead retention members relative to each other; and
disposing the cover over the base.

14. The method of claim 13, wherein inserting the locking member comprises separating the two lead retention members using the wedge element of the locking member and locking the two lead retention members by inserting the two pins of the locking member into the receiving openings in the two lead retention members.

15. The method of claim 13, wherein inserting the two lead retention members comprises fitting a ridge defined in the sidewall of the base into a circumferential groove in each of the two lead retention members.

16. The method of claim 13, wherein inserting the two lead retention members comprises rotating the two lead retention members to position a lead extending through the base between the lead engagement surfaces of the two lead retention members.

* * * * *